United States Patent [19]
Kindsvogel et al.

[11] Patent Number: 6,060,309
[45] Date of Patent: May 9, 2000

[54] IMMUNE MEDIATORS AND RELATED METHODS

[75] Inventors: Wayne Kindsvogel, Seattle, Wash.; Eva Pia Reich, Palo Alto, Calif.; Jane A. Gross, Seattle, Wash.

[73] Assignee: Anergen, Inc., Redwood City, Calif.

[21] Appl. No.: 08/855,925

[22] Filed: May 14, 1997

Related U.S. Application Data

[63] Continuation of application No. 08/483,241, Jun. 7, 1995, abandoned.

[51] Int. Cl.[7] .............................. C12N 5/06; C07K 16/28; C07K 17/14
[52] U.S. Cl. ...................... 435/325; 530/350; 530/387.1; 530/388.2; 530/388.22; 530/388.75; 530/389.6; 530/391.1
[58] Field of Search .......................... 435/325; 530/387.1, 530/388.2, 388.22, 388.75, 389.6, 391.1, 350

[56] References Cited

PUBLICATIONS

Zhang et al., *J. Exp. Med.* 179: 973–984, 1994.
Pette et al., *Proc. Natl. Acad. Sci. USA* 87: 7968–7972, 1990.
Wucherpfenning et al., *J. Immunol.* 153(12):5581–5592, 1994.
Petted et al., *Neurology* 40: 1770–1776, 1990.
Lohmann et al., *Lancet* 343: 1607–1608, 1994.
Honeyman et al., *J. Exp. Med.* 177: 535–540, 1993.
Harrison et al., *Lancet* 341: 1365–1369, 1993.
Atkinson et al., *J. Clin. Invest.* 94: 2125–2129, 1994.
Tian et al., *J. Exp. Med.* 180: 1979–1984, 1994.
Atkinson et al., *Lancet* 339: 458–459, 1992.
Martin et al., *J. Exp. Med.* 173: 19–24, 1991.
Vliet et al., *Eur. J. Immunol.* 19: 213–216, 1989.
Peakman et al., *Autoimmunity* 17: 31–39, 1994.
Roep et al., *Lancet* 337: 1439–1441, 1991.
Honeyman, M. C. et al. *J. Ecp. Med.* 177: 535–540, Feb. 1993.
Peakman, M. et al. Autoimmunity 17: 31–39, Jan. 1994.
Van den Elsen, J.H. et al. Journal of Immunological Methods 112: 15–22, 1988.
Coligan, J. E. et al. (Eds.), Current Protocols in Immunology, Greene Publishing Associates and Wiley–Interscience, New York, NY, PP. 7.1.3 and 7.19.1–17.19.5, 1991.
Zhang, J. et al. J. Exp. Med. 179: 973–984, Mar. 1994.

*Primary Examiner*—David Saunders
*Assistant Examiner*—F. Pierre VanderVegt
*Attorney, Agent, or Firm*—Townsend and Townsend and Crew LLP

[57] ABSTRACT

A method for preparing a responder cell clone that proliferates when combined with a selected antigenic peptide presented by a stimulator cell is disclosed. CD56 negative, CD8 negative responder cells are isolated from peripheral blood mononucleocytes and stimulated with pulsed or primed stimulator cells. Responder cell clones from prediabetic or new onset diabetic patients which are specific for GAD peptides are also disclosed.

4 Claims, No Drawings

```
                       SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
         (A) LENGTH: 20 amino acids
         (B) TYPE: amino acid
         (C) STRANDEDNESS:
         (D) TOPOLOGY: linear (ii) MOLECULE TYPE: peptide (ix) FEATURE:
         (A) NAME/KEY: Modified-site
         (B) LOCATION: 20
         (D) OTHER INFORMATION: /product= "OTHER"
             /note= "Xaa = glycinamine"

(xi) SEQUENCE DESCRIPTION: SEQ ID NO:1:

Asn Met Tyr Ala Met Met Ile Ala Arg Phe Lys Met Phe Pro Glu Val
1               5                  10                  15

Lys Glu Lys Xaa
            20

(2) INFORMATION FOR SEQ ID NO:2:

(i) SEQUENCE CHARACTERISTICS:
         (A) LENGTH: 20 amino acids
         (B) TYPE: amino acid
         (C) STRANDEDNESS:
         (D) TOPOLOGY: linear (ii) MOLECULE TYPE: peptide
```

```
    (ix) FEATURE:
         (A) NAME/KEY: Modified-site
         (B) LOCATION: 20
         (D) OTHER INFORMATION: /product= "OTHER"
              /note= "Xaa = lysinamide"

(xi) SEQUENCE DESCRIPTION: SEQ ID NO:2:

Val Pro Pro Ser Leu Arg Thr Leu Glu Asp Asn Glu Glu Arg Met Ser
1               5                  10                  15

Arg Leu Ser Xaa
            20

(2) INFORMATION FOR SEQ ID NO:3:

(i) SEQUENCE CHARACTERISTICS:
         (A) LENGTH: 20 amino acids
         (B) TYPE: amino acid
         (C) STRANDEDNESS:
         (D) TOPOLOGY: linear (ii) MOLECULE TYPE: peptide (ix) FEATURE:
         (A) NAME/KEY: Modified-site
         (B) LOCATION: 20
         (D) OTHER INFORMATION: /product= "OTHER"
              /note= "Xaa = threoninamide"

(xi) SEQUENCE DESCRIPTION: SEQ ID NO:3:

Ser Arg Leu Ser Lys Val Ala Pro Val Ile Lys Ala Arg Met Met Glu
1               5                  10                  15

Tyr Gly Thr Xaa
            20

(2) INFORMATION FOR SEQ ID NO:4:

(i) SEQUENCE CHARACTERISTICS:
         (A) LENGTH: 6 amino acids
         (B) TYPE: amino acid
         (C) STRANDEDNESS:
         (D) TOPOLOGY: linear (ii) MOLECULE TYPE: peptide (xi) SEQUENCE DESCRIPTION: SEQ ID NO:4:

Gly Gly Ser Gly Gly Ser
1               5

(2) INFORMATION FOR SEQ ID NO:5:

(i) SEQUENCE CHARACTERISTICS:
         (A) LENGTH: 6 amino acids
         (B) TYPE: amino acid
         (C) STRANDEDNESS:
         (D) TOPOLOGY: linear (ii) MOLECULE TYPE: peptide (xi) SEQUENCE DESCRIPTION: SEQ ID NO:5:

Asp Glu Asn Val Val His
1               5

(2) INFORMATION FOR SEQ ID NO:6:

(i) SEQUENCE CHARACTERISTICS:
         (A) LENGTH: 14 amino acids
         (B) TYPE: amino acid
```

-continued

```
         (C) STRANDEDNESS:
         (D) TOPOLOGY: linear (ii) MOLECULE TYPE: peptide (xi) SEQUENCE DESCRIPTION: SEQ ID NO:6:

Phe Phe Lys Asn Ile Val Thr Pro Arg Thr Ile Pro Pro Ser
1               5                  10

(2) INFORMATION FOR SEQ ID NO:7:

(i) SEQUENCE CHARACTERISTICS:
         (A) LENGTH: 5 amino acids
         (B) TYPE: amino acid
         (C) STRANDEDNESS:
         (D) TOPOLOGY: linear (ii) MOLECULE TYPE: peptide (xi) SEQUENCE DESCRIPTION: SEQ ID NO:7:

Gly Gly Gly Ser Gly
1               5

(2) INFORMATION FOR SEQ ID NO:8:

(i) SEQUENCE CHARACTERISTICS:
         (A) LENGTH: 5 amino acids
         (B) TYPE: amino acid
         (C) STRANDEDNESS:
         (D) TOPOLOGY: linear (ii) MOLECULE TYPE: peptide (xi) SEQUENCE DESCRIPTION: SEQ ID NO:8:

Gly Ala Ser Ala Gly
1               5
```

IMMUNE MEDIATORS AND RELATED METHODS

This is a continuation of application Ser. No. 08/483,241, filed Jun. 7, 1995, now abandoned.

BACKGROUND OF THE INVENTION

There is currently a great interest in developing pharmaceuticals based on the growing understanding of the structure and function of the major histocompatibility complex (MHC) antigens. These cell surface glycoproteins are known to play an important role in antigen presentation and in eliciting a variety of T cell responses to antigens.

T cells, unlike B cells, do not directly recognize antigens. Instead, an accessory cell must first process the antigen and present it in association with an MHC molecule in order to elicit an immunological response. The major function of MHC glycoproteins appears to be the binding and presentation of processed antigen in the form of short antigenic peptides.

In addition to binding foreign or "non-self" antigenic peptides, MHC molecules can also bind "self" peptides. If T lymphocytes then respond to cells presenting "self" or autoantigenic peptides, a condition of autoimmunity results. Over 30 autoimmune diseases are presently known, including myasthenia gravis (MG), multiple sclerosis (MS), systemic lupus erythematisus (SLE), rheumatoid arthritis (RA), insulin-dependent diabetes mellitus (IDDM), etc. Characteristic of these diseases is an attack by the immune system on the tissues of the victim. In non-diseased individuals, such attack does not occur because the immune system recognizes these tissues as "self". Autoimmunity results when the ability to recognize certain autoantigens as "self" is lacking.

Insulin-dependent diabetes mellitus (IDDM) is a disease resulting from the autoimmune destruction of the insulin-producing β-cells of the pancreas. Studies directed at identifying the autoantigen(s) responsible for β-cell destruction have identified several candidates, including insulin (Palmer et al., *Science* 222: 1337–1339, 1983), a poorly characterized islet cell antigen (Bottazzo et al, *Lancet* ii: 1279–1283, 1974) and a 64 kDa antigen that has been shown to be glutamic acid decarboxylase (Baekkeskov et al., *Nature* 298: 167–169 (1982); Baekkeskov et al., *Nature* 347: 151–156, 1990). Antibodies to glutamic acid decarboxylase (hereinafter referred to as "GAD") have been found to be present in patients prior to clinical manifestation of IDDM (Baekkeskov et al, *J. Clin. Invest.* 79: 926–934, 1987).

GAD catalyzes the rate-limiting step in the synthesis of c-aminobutyric acid (GABA), a major inhibitory neurotransmitter of the mammalian central nervous system. Little is known with certainty regarding the regulation of GAD activity or the expression of GAD genes. Despite its wide distribution in the brain, GAD protein is present in very small quantities and is very difficult to purify to homogeneity. GAD has multiple isoforms encoded by different genes. These multiple forms of the enzyme differ in molecular weight, kinetic properties, sequence (when known), and hydrophobic properties. For example, the presence of three different forms of GAD in porcine brain has been reported (Spink et al., *J. Neurochem.* 40: 1113–1119, 1983), as well as rour forms in rat brain (Spink et al., *Brain Res.* 421: 235–244, 1987). A mouse brain GAD (Huang et al., *Proc. Natl. Acad. Sci. USA* 87: 8491–8495, 1990) and a GAD clone isolated from feline brain (Kobayashi et al., *J. Neurosci.* 7: 2768–2772, 1987) have also been reported. At least two isomers of GAD have been reported in human brain (Chang and Gottlieb, *J. Neurosci.* 8: 2123–2130, 1988). A human pancreatic islet cell GAD has recently been characterized by molecular cloning (Lernmark et al., U.S. patent application Ser. No. 07/702,162; PCT publication WO 92/20811). This form of GAD is identical to one subsequently identified human brain isoform (Bu et al., *Proc. Natl. Acad. Sci. USA* 89: 2115–2119, 1992). A second GAD isoform identified in human brain is not present in human islets (Karlsen et al., *Diabetes* 41: 1355–1359, 1992).

Evidence suggests that GAD is the primary autoantigen responsible for initiating the β cell assault leading to diabetes both in humans and in animal models. Three peptides derived from mouse and human GAD65, peptide #17 sequence 246–266, peptide #34 sequence 509–528 and peptide #35 sequence 524–543, have been implicated as candidates for the autoantigen by their ability to induce a T cell response in mice (Kaufman et al., *Nature* 366: 69–71).

Current treatment for autoimmune disease and related conditions consists primarily of treating the symptoms, but not intervening in the etiology of the disease. Broad spectrum chemotherapeutic agents are typically employed, which agents are often associated with numerous undesirable side effects. Therefore, there is a need for compounds capable of selectively suppressing autoimmune responses by blocking MHC binding, thereby providing a safer, more effective treatment. In addition, such selective immunosuppressive compounds are needed in the treatment of non-autoimmune diseases, such as graft versus host disease (GVHD) or various allergic response. For instance, chronic GVHD patients frequently present conditions and symptoms similar to certain autoimmune diseases.

The inadequate treatments presently available illustrate the urgent need to identify new agents that block MHC-restricted immune responses, but avoid undesirable side effects such as nonspecific suppression of an individual's overall immune response. A desirable approach to treating autoimmune diseases and other pathological conditions mediated by MHC is to use antagonists to block binding to the T cell receptor. The present invention fulfills such needs, and provides related advantages.

SUMMARY OF THE INVENTION

It is an object of the present invention to provide a method for preparing a responder cell clone that proliferates when combined with a selected antigenic peptide presented by a stimulator cell, comprising: isolating non-adherent, CD56-, CD8- cells that are reactive with the selected antigenic peptide, thereby forming responder cells; stimulating the responder cells with pulsed or primed stimulator cells; restimulating the stimulated responder cells to pulsed or primed stimulator cells; and isolating a responder cell clone.

Within one aspect of the invention, the responder cells are isolated from a prediabetic or new onset diabetic patient. Within another aspect, the responder cell clone is a T cell clone. Within yet another aspect, the selected antigenic peptide is a GAD peptide.

These and other aspects of the invention will become evident upon reference to the following detailed description.

DETAILED DESCRIPTION OF THE INVENTION

The major histocompatibility complex (MHC) is a region of highly polymorphic genes, divided into two classes, Class I and Class II, which are membrane associated and present antigen to T lymphocytes (T cells). MHC Class I and Class II are distinguished by the types of cells on which they are expressed and the subsets of T cells which recognize them. Class I MHC molecules (e.g., HLA-A, -B and -C molecules in the human system) are expressed on almost all nucleated cells and are recognized by cytotoxic T lymphocytes (CTL), which then destroy the antigen-bearing cells. Class II MHC molecules (HLA-DP, Q and -DR, for example, in humans) are expressed primarily on the surface of antigen presenting cells such as B lymphocytes, dendritic cells, macrophages, and the like. Class II is recognized by $CD4^+$ T helper lymphocytes ($T_H$). $T_H$ induce proliferation of both B and T lymphocytes, thus amplifying the immune response to the particular antigenic peptide that is displayed (Takahashi, *Macrobiol. Immunol.*, 37: 1–9, 1993). Two distinct antigen processing pathways are associated with the two MHC classes. Intracellular antigens, synthesized inside of the cell, such as from viral or newly synthesized cellular proteins, for example, are processed and presented by Class I MHC. Exogenous antigens, taken up by the antigen presenting cell (APC) from outside of the cell through endocytosis, are processed and presented by Class II MHC. After the antigenic material is proteolytically processed by the MHC-bearing cell, the resulting antigenic peptide forms a complex with the antigen binding groove of the MHC molecule through various noncovalent associations. The MHC:peptide complex on the cell surface is recognized by a specific T cell receptor on a cytotoxic or helper T cell.

The MHC of humans (also referred to as human leukocyte antigens (HLA)) on chromosome 6 has three loci, HLA-A, HLA-B and HLA-C, the first two of which have a large number of alleles encoding alloantigens. An adjacent region known as HLA-D is subdivided into HLA-DR, HLA-DQ and HLA-DP. The HLA region is now known as the human MHC region, and is equivalent to the H-2 region in mice. HLA-A, -B and -C are homologous for mouse H-2K, -D, and -L and are the Class I MHC molecules. HLA-DP, -DQ and -DR resemble mouse I-A and I-E and are the Class II molecules. MHC glycoproteins of both classes have been isolated and characterized (see, *Fundamental Immunology*, 2d Ed., W. E. Paul (ed)., Ravens Press, N.Y., (1989), and Roitt et al., *Immunology*, 2d Ed., Gower Medical Publishing, London, (1989), which are both incorporated herein by reference).

Human MHC Class I molecules consist of a polymorphic type I integral membrane glycoprotein heavy chain of about 46 kD, noncovalently associated with a 12 kD soluble subunit, β2-microglobulin. The heavy chain consists of two distinct extracellular regions, the membrane distal, peptide binding region formed by the α1 and α2 domains, and the membrane proximal, CD8-binding region derived from the α3 domain. β-2 microglobulin is a single, compact immunogobulin-like domain that lacks a membrane anchor and exists either associated with the class I heavy chain or free in plasma (Germain and Margulies, *Annu. Rev. Immunol.*, 11: 403–50, 1993).

Human MHC Class II is a heterodimeric integral membrane protein. Each dimer consists of one α and one β chain in noncovalent association. The two chains are similar to each other with the α chain at 32–34 kd and the β chain 29–32 kd. Both polypeptide chains contain N-linked oligosaccharide groups and have extracellular amino termini and intracellular carboxy termini.

The extracellular portions of the α and β chain that comprise the class II molecule have been subdivided into two domains of about 90 amino acids each, called α1, α2, and β1, β2 respective. α2 and β2 each contain a disulfide-linked loop. The peptide-binding region of the class II molecule is formed by the interaction of the α1 and β2, which forms an open-ended, antigenic peptide-binding groove, made up of two α helices, and an eight stranded β pleated sheet platform.

The two Class II molecules are encoded on different MHC genes and are polymorphic (in Addas et al., *Cellular and Molecular Immunology* 2 Ed., W.B. Saunders Co., New York, 1994, which is incorporated by reference in its entirety).

The immunological properties of histocompatibility proteins are largely defined by the antigenic peptide that is bound to them. An antigenic peptide is one which contains an amino acid sequence recognized by immune cells e.g., T cells. Antigenic peptides for a number of autoimmune diseases are known. For example, in experimentally induced autoimmune diseases, antigens involved in pathogenesis have been characterized: in arthritis in rat and mouse, native type II collagen is identified in collagen-induced arthritis, and mycobacterial heat shock protein in adjuvant arthritis, (Stuart et al., *Ann. Rev. Immunol.* 2: 199–218, 1984; and van Eden et al., *Nature* 331: 171–173, 1988), thyroglobulin has been identified in experimental allergic thyroiditis (EAT) in mice (Marion et al., *J. Exp. Med.* 152: 1115–1120, 1988); acetyl-choline receptor (AChR) in experimental allergic myasthenia gravis (EAMG) (Lindstrom et al., *Adv. Immunol.* 42: 233–284, 1988); and mylein basic protein (MBP) and proteolipid protein (PLP) in experimental encephalomyelitis (EAE) in mouse and rat (Acha-Orbea et al., *Ann. Rev. Imm.* 7: 377–405, 1989). In addition, target antigens have been identified in humans: type-II collagen in human rheumatoid arthritis (Holoshitz et al., *Lancet* ii: 305–309, 1986) and acetyl choline receptor in myasthenia gravis (Linstrom et al., *Adv. Immunol.* 42: 233–284, 1988).

MHC molecules themselves can be used as antagonists to therapeutically block the binding of particular T cells and antigen presenting cells. In addition, the molecules can induce anergy, or proliferative nonreponsiveness, in targeted T cells. Production of a MHC molecule directed toward a desired autoimmune disease containing the antigenic peptide implicated for that autoimmune disease properly contained in the binding groove of that MHC molecule with out need for solublization or exogenous loading of an independently manufactured peptide would be particularly desirable.

Previous methods for producing desirable MHC Class II histocompatibility proteins have provided material that contains a mixture of antigenic peptides (Buus et al., *Science*, 242: 1045–1047, 1988; and Rudensky et al., *Nature*, 353: 622–627, 1991), which can be only partially loaded with a defined antigenic peptide (Watts and McConnel, *Proc. Natl. Acad. Sci. USA*, 83: 9660-, 1986; Buus et al., *Immunol. Rev.*, 98: 115-, and Ceppellini et al., *Nature*, 339: 392-, 1989). Various methods have been developed to produce heterodimers that do not present endogenous antigens (Stern and Wiley, *Cell* 68: 465–77; Ljunggren et al., *Nature*, 346: 476–80; and Schumacher et al., Cell, 62: 563–67) that can be loaded with a peptide of choice. Kozono et al., have described production of soluble murine Class II, I-$E^{dk}$ and I-$A^d$, each with a peptide attached by a linker to the N terminus of the β chain. Ignatowicz et al., *J. Imm.* 154: 38–62, 1995) have expressed membrane bound I-$A^d$ with peptide attached. These methods incorporate the use of both membrane bound heterodimer and soluble heterodimer. As used herein, a soluble heterodimer is one that is not membrane-associated MHC and has never been membrane associated and wherein the polypeptides contained within the heterodimer do not contain an amino acid sequence acting as a transmembrane domain or as a cytoplasmic domain.

The present invention provides a soluble, fused MHC heterodimer which contains an antigenic peptide covalently attached to the amino terminal portion of an α or β chain of MHC through a peptide linkage, which may be attached to another portion of an α or β chain. The α chain portion can include, α1 or α2 independent of the other, α1α2, or α1 and α2 in tandem, or joined together through an intervening peptide linkage. The β chain portion can include, β1 or β2 independent, β1β2, β1 and β2 in tandem, or joined together through an intervening peptide linkage. Combinations of α1, α, β1 and β2 can also be created through flexible linkers, such as β1α1, or β1α1α2, for example.

Linkers of the current invention may be from 5 to 25 amino acids in length, depending on the molecular model of the MHC complex. Preferably, flexible linkers are made of repeating Gly residues separated by a Ser residue to permit a random, flexible motion. This flexibility accommodates positioning of the α and β segments to properly configure the binding groove, and also allows for maximum positioning of the peptide in the groove. Linker position and length can be modeled based on the crystal structure of MHC Class II molecules (Brown et al., *Nature* 364: 33–39) where α1 and β1 are assembled to form the peptide binding groove. Linkers joining segments of the α and β chains together are based on the geometry of the region in the hypothetical binding site and the distance between the C terminus and the N terminus of the relevant segments. Molecular modeling based on the X-ray crystal structure of Class II (Stern et al., *Nature* 368: 215–221 1994) dictates the length of linkers joining antigenic peptide, α chain segments and β chain segments.

The soluble, fused heterodimer MHC:peptide complexes of the present invention can incorporate cDNA from any allele that confers susceptibility to a specific autoimmune disease. Specific autoimmune diseases are correlated with specific MHC types. Specific haplotypes have been associated with many of the autoimmune diseases. For example, HLA-DR2$^+$ and HLA-DR3$^+$ individuals are at a higher risk than the general population to develop Systemic Lupus Erythematosus (SLE) (Reinertsen et al., *N. Engl. J. Med.*, 299: 515-, 1970). Myasthenia gravis has been linked to HLA-D (Safenberg et al., *Tissue Antigens* 12: 136- , 1978; McDevitt et al., *Arth. Rheum.* 20: 59- 1977). Susceptibility to rheumatoid arthritis is associated with HLA-D/DR in humans. Methods for identifying which alleles, and subsequently which MHC-encoded polypeptides, are associated with an autoimmune disease are known in the art. Exemplary alleles include for IDDM include DR4, DQ8, DR3, DQ2.

The amino acid sequence of each of a number of Class I and Class II proteins are known, and the genes or cDNAs have been cloned. Thus, these nucleic acids can be used to express MHC polypeptides. If a desired MHC gene or cDNA is not available, cloning methods known to those skilled in the art may be used to isolate the genes. One such method that can be used is to purify the desired MHC polypeptide, obtain a partial amino acid sequence, synthesize a nucleotide probe based on the amino acid sequence, and use the probe to identify clones that harbor the desired gene from a cDNA or genomic library.

An ELISA (Enzyme-linked Immunosorbent Assay) can be used to measure concentration and confirm correct folding of the soluble, fused heterodimer molecules. This assay can be used with either whole cells, solublized MHC, removed from the cell surface; or free soluble, fused heterodimer molecules of the current invention. In an exemplary ELISA, an antibody that detects the recombinant MHC haplotype is coated onto wells of a microtiter plate. In a preferred embodiment, the antibody is L243, a monoclonal antibody that recognizes only correctly folded HLA-DR MHC dimers. One of skill in the art will recognize that other MHC Class II-specific antibodies are known and available. Alternatively, there are numerous routine techniques and methodologies in the field for producing antibodies (for example, Hurrell, J. G. R. (ed)., *Monoclonal Hybridoma Antibodies: Techniques and Applications*, CRC Press Inc., Boca Raton, Fla., 1982), if an appropriate antibody for a particular haplotype does not exist. Anti-MHC Class II antibodies can also be used to purify Class II antibodies can also be used to purify Class II molecules through techniques such as affinity chromatography, or as a marker reagent to detect the presence of Class II molecules on cells or in solution. Such antibodies are also useful for western analysis or immunoblotting, particularly of purified cell secreted material. Polyclonal, affinity purified polyclonal, monoclonal and single chain antibodies are suitable for use in this regard. In addition, proteolytic and recombinant fragments and epitope binding domains can be used herein. Chimeric, humanized, veneered, CDR-replaced, reshaped or other recombinant whole or partial antibodies are also suitable.

In the ELISA format, bound MHC molecules can be detected using an antibody or other binding moiety capable of binding MHC molecules. This binding moiety or antibody may be tagged with a detectable label, or may be detected using a detectably labeled secondary antibody or binding reagent. Detectable labels or tags are known in the art, and include fluorescent, colorimetric and radiolabels, for instance.

The in vitro assay is an antigen-specific responder cell activation assay. Briefly, a soluble, fused heterodimer MHC molecule containing antigenic peptide in the peptide binding groove was mixed with responder cells, preferably peripheral blood mononuclear (PBMN) cells (a heterogeneous population including B and T lymphocytes, monocytes and dendritic cells), PBMN lymphocytes, freshly isolated T lymphocytes, in vivo primed splenocytes, cultured T cells, or established T cell lines, clones or hybridomas. Responder cells from mammals immunized with, or having a demonstrable cellular immune response to, the antigenic peptide are particularly preferred.

Subsequently, these responder cells are combined with stimulator cells (antigen presenting cells; APCs) that have been pulsed or primed with the same antigenic peptide. In a preferred embodiment, the stimulator cells are antigenic peptide-presenting cells, such as peripheral blood mononuclear (PBMN) cells, PBMN cells that have been depleted of lymphocytes, appropriate antigenic peptide-presenting cell lines or clones (such as EBV-transformed B cells), or in vivo or in vitro primed or pulsed splenocytes. Stimulator cells from mammals immunized with, or having a demonstrable cellular immune response to, the antigenic peptide are particularly preferred. For certain assay formats, it is preferred to inhibit the proliferation of stimulator cells prior to mixing with responder cells. This inhibition may be achieved by exposure to gamma irradiation or to an antimitotic agent, such as mitomycin C, for instance. Appropriate negative controls are also included (no soluble, fused heterodimer MHC/peptide; no APCs; and the like).

After an approximately 72 hour incubation, the activation of responder cells in response to the stimulator cells is measured. In a preferred embodiment, responder cell activation is determined by measuring proliferation using $^3$H-thymidine uptake (Crowley et al., *J. Immunol. Meth.* 133: 55–66, 1990). Alternatively, responder cell activation can be measured by the production of cytokines, such as IL-2, or by determining the presence of responder cell-specific, and particularly T cell-specific, activation markers. Cytokine production can be assayed by testing the ability of the stimulator + responder cell culture supernatant to stimulate growth of cytokine-dependent cells. Responder cell- or T cell-specific activation markers may be detected using antibodies specific for such markers.

Preferably, the soluble, fused heterodimer induces non-responsiveness (for example, anergy) in the antigenic peptide-reactive responder cells. In addition to MHC class II-peptide recognition, responder cell activation requires the involvement of co-receptors on the stimulator cell (the APC) that have been stimulated with co-stimulatory molecules. By blocking or eliminating stimulation of such co-receptors (for instance, by exposing responder cells to purified soluble MHC Class II:peptide complexes, by blocking with anti-receptor or anti-ligand antibodies, or by "knocking out" the gene(s) encoding such receptors), responder cells can be rendered non-responsive to antigen or to antigen:MHC Class II complexes.

In a preferred embodiment, responder cells are obtained from a patient manifesting an autoimmune disease or syndrome. Alternatively, autoantigen-reactive T cell clones are preferred responder cells. In another preferred embodiment, stimulator cells are obtained from a patient manifesting an autoimmune disease or syndrome. Alternatively, APC cell lines or clones that are able to appropriately process and/or present autoantigen to responder cells are preferred stimulator cells. In a particularly preferred embodiment, responder and stimulator cells are obtained from patients with diabetes or multiple sclerosis.

At this point, the responder T cells can be selectively amplified and/or stimulated, thereby producing a subset of T cells that are specific for the antigenic peptide. For instance, antigenic peptide-reactive responder cells may be selected by flow cytometry, and particularly by fluorescence activated cell sorting. This subset of responder cells can be maintained by repetitive stimulation with APCs presenting the same antigenic peptide. Alternatively, responder cell clones can be established from this responder cell subset. Further, this subset of responder cells can be used to map epitopes of the antigenic peptide and the protein from which it is derived.

Similar assays and methods can be developed for and used in animal models of diseases mediated by MHC Class II:peptide complexes. For instance, a polynucleotide encoding I-A$^{g7}$ MHC Class II molecules of NOD mice, a model system for insulin-dependent diabetes mellitus (IDDM), can be combined with autoantigenic peptides of GAD to study induction of non-responsiveness in the animal model. When compared to human/patient studies, such animal model assays and methods will permit better identification of the strengths and limitations of the model system.

Soluble, fused heterodimer:peptide complex can be tested in vivo in a number of animal models of autoimmune disease. For example, NOD mice are a spontaneous model of IDDM. Treatment with the soluble, fused heterodimer complex prior to or after onset of disease can be monitored by assay of urine glucose levels in the NOD mouse, as well as by in vitro T cell proliferation assays to assess reactivity to known autoantigens (see Kaufman et al., *Nature* 366: 69–72, 1993, for example). Alternatively, induced models of autoimmune disease, such as EAE, can be treated with relevant soluble, fused heterodimer:peptide complex. Treatment in a preventive or intervention mode can be followed by monitoring the clinical symptoms of EAE.

The NOD mouse strain (H-2K$^d$D$^b$) is a murine model for autoimmune IDDM. In NOD mice, the disease is characterized by anti-islet cell antibodies, severe insulitis, and evidence for autoimmune destruction of beta-cells (see, for instance, Kanazawa et al., *Diabetologia* 27: 113, 1984). The disease can be passively transferred with lymphocytes and prevented by treatment with cyclosporin-A (Ikehara et al., *Proc. Natl. Acad. Sci. USA* 82: 7743, 1985; Mori et al., *Diabetologia* 29: 244, 1986). Untreated animals develop profound glucose intolerance and ketosis, and succumb within weeks of the onset of the disease. Seventy to ninety percent of females and 20–30% of males develop diabetes within the first six months of life. Breeding studies have defined at least two genetic loci responsible for disease susceptibility, one of which maps to the MHC. Characterization of NOD class II antigens at both the serological and molecular level suggest that the susceptibility to autoimmune disease is linked to I-A$^B$ (Acha-Orbea and McDevitt, *Proc. Natl. Acad. Sci. USA* 84: 235, 1987).

Prokaryotes that are useful as host cells, according to the present invention, most frequently are represented by various strains of *E. coli*. However, other microbial strains can also be used, such as bacilli, for example *Bacillus subtilis*, various species of Pseudomonas, or other bacterial strains.

According to the invention, the soluble, fused heterodimer molecules are expressed from recombinantly engineered nucleotide sequences that encode the soluble, fused heterodimer polypeptides by operably linking the engineered nucleic acid coding sequence to signals that direct gene expression in prokaryotes. A nucleic acid is "operably linked" when it is placed into a functional relationship with another nucleic acid sequence. For instance, a promoter or enhancer is operably linked to a coding sequence if it effects the transcription of the sequence. Generally, operably linked means that the nucleic acid sequences being linked are contiguous and, where necessary to join two protein coding regions, contiguous and in reading frame.

The genes encoding the soluble, fused heterodimer molecules may be inserted into an "expression vector", "cloning vector", or "vector", terms which are used interchangeably herein and usually refer to plasmids or other nucleic acid molecules that are able to replicate in a chosen host cell. Expression vectors may replicate autonomously, or they can replicate by being inserted into the genome of the host cell, by methods well known in the art. Vectors that replicate autonomously will have an origin of replication or autonomous replicating sequence (ARS) that is functional in the chosen host cell(s).

Plasmid vectors that contain replication sites and control sequences derived from a species compatible with the chosen host are used. For example, *E. coli* is typically transformed using derivatives of pBR322, a plasmid derived from *E. coli* species by Bolivar Et al., *Gene* 2: 95 1977. Often, it is desirable for a vector to be usable in more than one host cell, e.g., in *E. coli* for cloning and construction, and in a Bacillus cell for expression.

The expression vectors typically contain a transcription unit or expression cassette that contains all the elements required for the expression of the DNA encoding the MHC molecule in the host cells. A typical expression cassette contains a promoter operably linked to the DNA sequence encoding a MHC polypeptide and a ribosome binding site. The promoter is preferably positioned about the same distance from the heterologous transcription start site as it is from the transcription start site in its natural setting. As is known in the art, however, some variation in this distance can be accommodated without loss of promoter function. In addition to a promoter sequence, the expression cassette can also contain a transcription termination region downstream of the structural gene to provide for efficient termination. The termination region may be obtained from the same gene as the promoter sequence of may be obtained from a different gene.

Commonly used prokaryotic control sequences which are defined herein to include promoters for transcription initiation, optionally with an operator, along with ribosome binding site sequences, include such commonly used promoters as the betalactamase (penicillinase) and lactose (lac) promoter systems (Change et al., Nature 198: 1056, 1977) and the tryptophan (trp) promoter system (Goeddel et al., Nucleic Acids Res. 8: 4057 1988) and the lambda-derived $P_L$ promoter and N-gene ribosome binding site (Shimatake et al., Nature 292: 128 1981). Any available promoter system that functions in prokaryotes can be used.

Either constitutive or regulate promoters can be used in the present invention. Regulated promoters can be advantageous because the host cells can be grown to high densities before expression of the MHC polypeptides is induced. High level expression of heterologous proteins slows cell growth in some situations. Regulated promoters especially suitable for use in E. coli include the bacteriophage lambda $P_L$ promoter, the hybrid trp-lac promoter (Amann et al., Gene 25: 167 1983;, and the bacteriophage T7 promoter.

For expression of MHC polypeptides in prokaryotic cells other than E. coli, a promoter that functions in the particular prokaryotic species is required. Such promoters can be obtained from genes that have been cloned from the species, or heterologous promoters can be used. For example, the hybrid trp-lac promoter functions in Bacillus in addition to E. coli.

A ribosome binding site (RBS) is also necessary for expression of MHC polypeptides in prokaryotes. An RBS in E. coli, for example, consists of a nucleotide sequence 3–9 nucleotides in length located 3–11 nucleotide upstream of the initiation codon (Shine and Dalgarno, Nature (1975) 254: 34; Steitz, In Biological regulation and development: Gene expression (ed. R. F. Goldberger), vol. 1, p. 349, 1979, Plenum Publishing, NY).

Translational coupling may be used to enhance expression. The strategy uses a short upstream open reading frame derived from a highly expressed gene native to the translational system, which is placed downstream of the promoter, and a ribosome binding site followed after a few amino acid codons by a termination codon. Just prior to the termination codon is a second ribosome binding site, and following the termination codon is a start codon for the initiation of translation. The system dissolves secondary structure in the RNA, allowing for the efficient initiation of translation. See Squires, et. al., (1988), J. Biol. Chem. 263: 16297–16302.

The MHC polypeptides can be expressed intracellularly, or can be secreted from the cell. Intracellular expression often results in high yields. However, some of the protein may be in the form of insoluble inclusion bodies. Although intracellularly produced MHC polypeptides of the present invention are active upon being harvested following cell lysis, the amount of soluble, active MHC polypeptide may be increased by performing refolding procedures (see, e.g., Sambrook et al., supra.; Marston et al., Bio/Technology (1984) 2: 800; Schoner et al., Bio/Technology (1985) 3: 151). More than one MHC polypeptide may be expressed in a single prokaryotic cell by placing multiple transcriptional cassettes in a single expression vector, or by utilizing different selectable markers for each of the expression vectors which are employed in the cloning strategy.

A second approach for expressing the MHC polypeptides of the invention is to cause the polypeptides to be secreted from the cell, either into the periplasm or into the extracellular medium. The DNA sequence encoding the MHC polypeptide is linked to a cleavable signal peptide sequence. The signal sequence directs translocation of the MHC polypeptide through the cell membrane. An example of a suitable vector for use in E. coli that contains a promoter-signal sequence unit is pTA1529, which has the E. coli phoA promoter and signal sequence (see e.g., Sambrook et al., supra.; Oka et al., Proc. Natl. Acad. Sci. USA (1985) 82: 7212; Talmadge et al., Proc. Natl. Acad. Sci. USA (1980) 77: 3988; Takahara et al., J. Biol. Chem. (1985) 260: 2670). Once again, multiple polypeptides can be expressed in a single cell for periplasmic association.

The MHC polypeptides of the invention can also be produced as fusion proteins. This approach often results in high yeilds, because normal prokaryotic control sequences direct transcription and translation. In E. coli, lacZ fusions are often used to express heterologous proteins. Suitable vectors are readily available, such as the pUR, pEX, and pMR100 series (see, e.g., Sambrook et al., supra.). For certain applications, it may be desirable to cleave the non-MHC amino acids from the fusion protein after purification. This can be accomplished by any of several methods known in the art, including cleavage by cyanogen bromide, a protease, or by Factor X, (see, e.g. Sambrook et al., supra.; Itakura et al., Science (1977) 198: 1056; Goeddel et al., Proc. Natl. Acad. Sci. USA (1979) 76: 106; Nagai et al., Nature (1984) 309: 810; Sung et al., Proc. Natl. Acad. Sci. USA (1986) 83: 561). Cleavage sites can be engineered into the gene for the fusion protein at the desired point of cleavage.

A preferred system for obtaining recombinant proteins from E. coli which maintains the integrity of their N-termini has been described by Miller et al. Biotechnology 7: 698–704 (1989). In this system, the gene of interest is produced as a C-terminal fusion to the first 76 residues of the yeast ubiquitin gene containing a peptidase cleavage site. Cleavage at the junction of the two moieties results in production of a protein having an intact authentic N-terminal reside.

The vectors containing the nucleic acids that code for the MHC polypeptide are transformed into prokaryotic host cells for expression. "Transformation" refers to the introduction of vectors containing the nucleic acids of interest directly into host cells by well known methods. The particular procedure used to introduce the genetic material into the host cell for expression of the MHC polypeptide is not particularly critical. Any of the well known procedures for introducing foreign nucleotide sequences into host cells may be used. It is only necessary that the particular host cell utilized be capable of expressing the gene.

Transformation methods, which vary depending on the type of host cell, include electroporation; transfection employing calcium chloride, rubidium chloride calcium phosphate, or other substances; microprojectile bombardment; infection (where the vector is an infectious agent); and other methods. See, generally, Aambrook et al., (1989)

supra, and Current Protocols in Molecular Biology, supra. Reference to cells into which the nucleic acids described above have been introduced is meant to also include the progeny of such cells. Transformed prokaryotic cells that contain expression vectors for expressing MHC polypeptides are also included in the invention.

After standard transfection or transformation methods are used to produce prokaryotic cell lines that express large quantities of the MHC polypeptide, the polypeptide is then purified using standard techniques. See, e.g., Colley et al. (1989) J. Chem. 64: 17619–17622; and Methods in Enzymology, "Guide to Protein Purification", M. Deutscher, ed. Vol. 182 (1990). The recombinant cells are grown and the MHC polypeptide is expressed. The purification protocol will depend upon whether the MHC polypeptide is expressed intracellularly, into the periplasm, or secreted from the cell. For intracellular expression, the cells are harvested, lysed, and the MHC polypeptide is recovered from the cell lysate (Sambrook et al., supra.). Periplasmic MHC polypeptide is released from the periplasm by standard techniques (Sambrook et al., supra.). If the MHC polypeptide is secreted from the cells, the culture medium is harvested for purification of the secreted protein. The medium is typically clarified by centrifugation or filtration to remove cells and cell debris.

The MHC polypeptides can be concentrated by adsorption to any suitable resin (such as, for example, CDP-Sepharose=, Asialoprothrombin-Sepharose 4B, or Q Sepharose, or by use of ammonium sulfate fractionation, polyethylene glycol precipitation, or by ultrafiltration. Other means known in the art may be equally suitable.

Further purification of the MHC polypeptides can be accomplished by standard techniques, for example, affinity chromatography, ion exchange chromatography, sizing chromatography, or other protein purification techniques used to obtain homogeneity. The purified proteins are then used to produce pharmaceutical compositions, as described below.

DNA constructs may also contain DNA segments necessary to direct the secretion of a polypeptide or protein of interest. Such DNA segments may include at least one secretory signal sequence. Secretory signal sequences, also called leader sequences, prepro sequences and/or pre sequences, are amino acid sequences that play a role in secretion of mature polypeptides or proteins from a cell. Such sequences are characterized by a core of hydrophobic amino acids and are typically (but not exclusively) found at the amino termini of newly synthesized proteins. Very often the secretory peptide is cleaved from the mature protein during secretion. Such secretory peptides contain processing sites that allow cleavage of the secretory peptide from the mature protein as it passes through the secretory pathway. A preferred processing site is a dibasic cleavage site, such as that recognized by the *Saccharomyces cerevisiae* KEX2 gene. A particularly preferred processing site is a Lys-Arg processing site. Processing sites may be encoded within the secretory peptide or may be added to the peptide by, for example, in vitro mutagenesis.

Preferred secretory signals include the α factor signal sequence (prepro sequence: Kurjan and Herskowitz, Cell 30: 933–943, 1982; Kurjan et al., U.S. Pat. No. 4,546,082; Brake, EP 116,201), the PHO5 signal sequence (Beck et al., WO 86/00637), the BAR1 secretory signal sequence (MacKay et al., U.S. Pat. No. 4,613,572; MacKay, WO 87/002670), the SUC2 signal sequence (Carlsen et al., *Molecular and Cellular Biology* 3: 439–447, 1983), the a-1-antitrypsin signal sequence (Kurachi et al., *Proc. Natl. Acad. Sci. USA* 78: 6826–6830, 1981), the a-2 plasmin inhibitor signal sequence (Tone et al., *J. Biochem. (Tokyo)* 102: 1033–1042, 1987) and the tissue plasminogen activator signal sequence (Pennica et al., *Nature* 301: 214–221, 1983). Alternately, a secretory signal sequence may be synthesized according to the rules established, for example, by von Heinje (*European Journal of Biochemistry* 133: 17–21, 1983; *Journal of Molecular Biology* 184: 99–105, 1985; *Nucleic Acids Research* 14: 4683–4690, 1986). A particularly preferred signal sequence is the synthetic signal LaC212 spx (1–47)—ERLE described in WO 90/10075, which is incorporated by reference herein in its entirety.

Secretory signal sequences may be used singly or may be combined. For example, a first secretory signal sequence may be used in combination with a sequence encoding the third domain of barrier (described in U.S. Pat. No. 5,037,243, which is incorporated by reference herein in its entirety). The third domain of barrier may be positioned in proper reading frame 3' of the DNA segment of interest or 5' to the DNA segment and in proper reading frame with both the secretory signal sequence and a DNA segment of interest.

The choice of suitable promoters, terminators and secretory signals is well within the level of ordinary skill in the art. Methods for expressing cloned genes in *Saccharomyces cerevisiae* are generally known in the art (see, "Gene Expression Technology," *Methods in Enzymology*, Vol. 185, Goeddel (ed.), Academic Press, San Diego, Calif., 1990 and "Guide to Yeast Genetics and Molecular Biology," *Methods in Enzymology*, Guthrie and Fink (eds.), Academic Press, San Diego, Calif., 1991; which are incorporated herein by reference). Proteins of the present invention can also be expressed in filamentous fungi, for example, strains of the fungi Aspergillus (McKnight et al., U.S. Pat. No. 4,935,349, which is incorporated herein by reference). Expression of cloned genes in cultured mammalian cells and in *E. coli*, for example, is discussed in detail in Sambrook et al. (*Molecular Cloning: A Laboratory Manual, Second Edition*, Cold Spring Harbor, N.Y., 1989; which is incorporated herein by reference). As would be evident to one skilled in the art, one could express the proteins of the instant invention in other host cells such as avian, insect and plant cells using regulatory sequences, vectors and methods well established in the literature.

In yeast, suitable yeast vectors for use in the present invention include YRp7 (Struhl et al., *Proc. Natl. Acad. Sci. USA* 76: 1035–1039, 1978), YEp13 (Broach et al., *Gene* 8: 121–133, 1979), POT vectors (Kawasaki et al, U.S. Pat. No. 4,931,373, which is incorporated by reference herein), pJDB249 and pJDB219 (Beggs, *Nature* 275: 104–108, 1978) and derivatives thereof. Preferred promoters for use in yeast include promoters from yeast glycolytic genes (Hitzeman et al., *J. Biol. Chem.* 255: 12073–12080, 1980; Alber and Kawasaki, *J. Mol. Appl. Genet.* 1: 419–434, 1982; Kawasaki, U.S. Pat. No. 4,599,311) or alcohol dehydrogenase genes (Young et al., in *Genetic Engineering of Microorganisms for Chemicals*, Hollaender et al., (eds.), p. 355, Plenum, New York, 1982; Ammerer, *Meth. Enzymol.* 101: 192–201, 1983). In this regard, particularly preferred promoters are the TPI1 promoter (Kawasaki, U.S. Pat. No. 4,599,311, 1986) and the ADH2-4$^c$ promoter (Russell et al., *Nature* 304: 652–654, 1983; Irani and Kilgore, U.S. patent application Ser. No. 07/784,653, CA 1,304,020 and EP 284 044, which are incorporated herein by reference). The expression units may also include a transcriptional terminator. A preferred transcriptional terminator is the TPI1 terminator (Alber and Kawasaki, ibid.).

Yeast cells, particularly cells of the genus Saccharomyces, are a preferred host for use in producing compound of the current invention. Methods for transforming yeast cells with exogenous DNA and producing recombinant proteins therefrom are disclosed by, for example, Kawasaki, U.S. Pat. No. 4,599,311; Kawasaki et al., U.S. Pat. No. 4,931,373; Brake, U.S. Pat. No. 4,870,008; Welch et al., U.S. Pat. No. 5,037,743; and Murray et al., U.S. Pat. No. 4,845,075, which are incorporated herein by reference. Transformed cells are selected by phenotype determined by a selectable marker, commonly drug resistance or the ability to grow in the absence of a particular nutrient (e.g. leucine). A preferred vector system for use in yeast is the POT1 vector system disclosed by Kawasaki et al. (U.S. Pat. No. 4,931,373), which allows transformed cells to be selected by growth in glucose-containing media. A preferred secretory signal sequence for use in yeast is that of the *S. cerevisiae* MFα1 gene (Brake, ibid.; Kurjan et al., U.S. Pat. No. 4,546,082). Suitable promoters and terminators for use in yeast include those from glycolytic enzyme genes (see, e.g., Kawasaki, U.S. Pat. No. 4,599,311; Kingsman et al., U.S. Pat. No. 4,615,974; and Bitter, U.S. Pat. No. 4,977,092, which are incorporated herein by reference) and alcohol dehydrogenase genes. See also U.S. Pat. Nos. 4,990,446; 5,063,154; 5,139,936 and 4,661,454, which are incorporated herein by reference. Transformation systems for other yeasts, including *Hansenula polymorpha, Schizosaccharomyces pombe, Kluyveromyces lactis, Kluyveromyces fragilis, Ustilago maydis, Pichia pastoris, Pichia guillermondii* and *Candida maltosa* are known in the art. See, for example, Gleeson et al., *J. Gen. Microbiol.* 132: 3459–3465, 1986; Cregg, U.S. Pat. No. 4,882,279; and Stroman et al., U.S. Pat. No. 4,879,231.

Other fungal cells are also suitable as host cells. For example, Aspergillus cells may be utilized according to the methods of McKnight et al., U.S. Pat. No. 4,935,349, which is incorporated herein by reference. Methods for transforming *Acremonium chrysogenum* are disclosed by Sumino et al., U.S. Pat. No. 5,162,228, which is incorporated herein by reference. Methods for transforming Neurospora are disclosed by Lambowitz, U.S. Pat. No. 4,486,533, which is incorporated herein by reference.

Host cells containing DNA constructs of the present invention are then cultured to produce the heterologous proteins. The cells are cultured according to standard methods in a culture medium containing nutrients required for growth of the particular host cells. A variety of suitable media are known in the art and generally include a carbon source, a nitrogen source, essential amino acids, vitamins, minerals and growth factors. The growth medium will generally select for cells containing the DNA construct by, for example, drug selection or deficiency in an essential nutrient which is complemented by a selectable marker on the DNA construct or co-transfected with the DNA construct.

Yeast cells, for example, are preferably cultured in a chemically defined medium, comprising a non-amino acid nitrogen source, inorganic salts, vitamins and essential amino acid supplements. The pH of the medium is preferably maintained at a pH greater than 2 and less than 8, preferably at pH 6.5. Methods for maintaining a stable pH include buffering and constant pH control, preferably through the addition of sodium hydroxide. Preferred buffering agents include succinic acid and Bis-Tris (Sigma Chemical Co., St. Louis, Mo.). Yeast cells having a defect in a gene required for asparagine-linked glycosylation are preferably grown in a medium containing an osmotic stabilizer. A preferred osmotic stabilizer is sorbitol supplemented into the medium at a concentration between 0.1 M and 1.5 M, preferably at 0.5 M or 1.0 M. Cultured mammalian cells are generally cultured in commercially available serum-containing or serum-free media. Selection of a medium appropriate for the particular host cell used is within the level of ordinary skill in the art.

Methods for introducing exogenous DNA into mammalian host cells include calcium phosphate-mediated transfection (Wigler et al., *Cell* 14: 725, 1978; Corsaro and Pearson, *Somatic Cell Genetics* 7: 603, 1981; Graham and Van der Eb, *Virology* 52: 456, 1973), electroporation (Neumann et al., *EMBO J.* 1: 841–845, 1982) and DEAE-dextran mediated transfection (Ausubel et al., (eds)., *Current Protocols in Molecular Biology*, John Wiley and Sons, Inc., NY, 1987), which are incorporated herein by reference. Cationic lipid transfection using commercially available reagents including the Boehringer Mannheim Transfection-Reagent (N-[1-(2,3-Dioleoyloxy)propyl]-N,N,N-trimethyl ammoniummethylsulfate; Boehringer Mannheim, Indianapolis, Ind.) or LIPOFECTIN reagent (N-[1-(2,3-dioleyloxy)propyl]-N,N,N-trimethylammonium chloride and dioeleoyl phosphatidylethanolamine; GIBCO-BRL, Gaithersburg, Md.) using the manufacturer-supplied directions, may also be used. The production of recombinant proteins in cultured mammalian cells is disclosed, for example, by Levinson et al., U.S. Pat. No. 4,713,339; Hagen et al., U.S. Pat. No. 4,784,950; Palmiter et al., U.S. Pat. No. 4,579,821; and Ringold, U.S. Pat. No. 4,656,134, which are incorporated herein by reference. Preferred cultured mammalian cells include the COS-1 (ATCC No. CRL 1650), COS-7 (ATCC No. CRL 1651), BHK (ATCC No. CRL 1632), BHK 570 (ATCC No. CRL 10314) and 293 (ATCC No. CRL 1573; Graham et al., *J. Gen. Virol.* 36: 59–72, 1977) cell lines. Additional suitable cell lines are known in the art and available from public depositories such as the American Type Culture Collection, Rockville, Md.

The polypeptides of the present invention can be purified by first isolating the polypeptides from the cells followed by conventional purification such as by ion-exchange and partition chromatography as described by, for example, Coy et al. (Peptides Structure and Function, Pierce Chemical Company, Rockford, Ill., pp 369–372, 1983), by reverse-phase chromatography as described, for example, by Andreu and Merrifield (*Eur. J. Biochem.* 164: 585–590, 1987), or by HPLC as described, for example, by Kofod et al. (*Int. J. Peptide and Protein Res.* 32: 436–440, 1988). Additional purification can be achieved by conventional chemical purification means, such as liquid chromatography, gradient centrifugation, and gel electrophoresis, among others. Methods of protein purification are known in the art (see generally, Scopes, R., *Protein Purification*, Springer-Verlag, NY 1982, which is incorporated by reference herein) and can be applied to the purification of the recombinant polypeptides described herein.

The peptides of the present invention can be synthesized by solid phase or solution phase methods conventionally used for the synthesis of peptides (see, for example, Merrifield, R. B., *J. Amer. Chem. Soc.* 85: 2149–54, 1963; Birr, C., *Aspects of the Merrifield Peptide Synthesis*, Springer-Verlag, Heidelberg, 1978; Carpino, L. A., Acc. Chem. Res. 6: 191–98, 1973; Kent S. B., *Ann. Rev. Biochem.* 57: 957–89, 1988; Gregg et al., *Int. J. Peptide Protein Res.* 35: 161–214, 1990; *The Peptides, Analysis, Synthesis, Biology*, Vols. 1, 2, 3, 5: Gross, E and Meinhofer, J. (eds.), Acad. Press, New York, 1979; and Stewart et al., *Solid Phase Peptide Synthesis*, 2nd. ed., Pierce Chem. Co., Rockford, Ill., 1984; which are incorporated herein by reference in their entirety.) The use of solid phase methodology is preferred. Briefly, an N-protected C-terminal amino acid residue is linked to an insoluble support such as divinylbenzene cross-linked polystyrene, polyacrylamide resin, Kieselguhr/polyamide (pepsyn K), controlled pore glass, cellulose, polypropylene membranes, acrylic acid-coated polyethylene rods or the like. Cycles of deprotection, neutralization (in the case of BOC chemistry, vide infra) and coupling of successive protected amino acid derivatives are used to link the amino acids from the C-terminus according to the amino acid sequence.

For some synthetic peptides, an FMOC strategy using an acid-sensitive resin may be used. Preferred solid supports in this regard are divinylbenzene cross-linked polystyrene resins, which are commercially available in a variety of functionalized forms, including chloromethyl resin, hydroxymethyl resin, paraacetamidomethyl resin, benzhydrylamine (BHA) resin, 4-methylbenzhydrylamine (MBHA) resin, oxime resins, 4-alkoxybenzyl alcohol resin (Wang resin), 4-(2',4'-dimethoxyphenylaminomethyl)-phenoxymethyl resin, 2,4-dimethoxybenzhydrylamine resin, and 4-(2',4'-dimethoxyphenyl-FMOC-aminomethyl)-phenoxyacetamidonorleucyl-MBHA resin (Rink amide MBHA resin). Acid sensitive resins, such as Sasrin and 2-chlorotrityl, are particularly preferred because they require mild acid cleavage, thus preventing possible cleavage of Aib-Pro bonds. In addition, acid-sensitive resins also provide C-terminal acids, if desired. A particularly preferred protecting group for α amino acids is base-labile 9-fluorenylmethoxycarbonyl (FMOC).

Suitable protecting groups for the side chain functionalities of amino acids chemically compatible with BOC (t-butyloxycarbonyl) and FMOC groups are well known in the art. When using FMOC chemistry, the following protected amino acid derivatives are preferred:Fmoc-Ala-OH, Fmoc-Arg(Pmc)-OH, Fmoc-Glu(OtBu)-OH, Fmoc-Gly-OH, Fmoc-Ile-OH, Fmoc-Leu-OH, Fmoc-Lys(BOc)-OH, Fmoc-Met-OH, Fmoc-Pro-OH, Fmoc-Ser(tBu)-OH, Fmoc-Thr(t-Bu)-OH, Fmoc-Tyr(tBu)-OH, Fmoc-Val-OH and Rink-amide-MBHA resin. The amino acid residues can be coupled by using a variety of coupling agents and chemistries known in the art, such as direct coupling with DIC (diisopropyl-carbodiimide), DCC (dicyclohexylcarbodiimide), BOP (benzotriazolyl-N-oxytrisdimethylaminophos-phonium hexafluorophosphate), PyBOP (benzotriazole-1-yl-oxy-tris-pyrrolidino phosphonium hexafluorophosphate), PyBrOP (bromo-tris-pyrrolidino-phosphonium hexafluorophosphate); via preformed symmetrical anhydrides; via active esters such as pentafluorophenyl esters; or via preformed HOBt (1-hydroxybenzotriazole) active esters or by using FMOC-amino acid fluoride and chlorides or by using FMOC-amino acid-N-carboxy anhydrides. Activation with HBTU ([2-(1H-benzotriazole-1-yl),1,1,3,3-tetramethyluronium hexafluorophosphate]) or HATU ([2-(1H-7-aza-benzotriazole-1-yl),1,1,3,3-tetramethyluronium hexafluorophosphate]) in the presence of HOBt or HOAt (7-azahydroxybenztriazole) is preferred.

The solid phase method can be carried out manually, although automated synthesis on a commercially available peptide synthesizer (e.g., Applied Biosystems 431A or the like) is preferred. Double coupling may also be used.

EXAMPLES

Example 1

Construction of a DNA Sequence Encoding a Soluble, Fused Heterodimer:Petide Complex Plasmid pLJ12 contains the MHC Class II β chain (DR1β*1501) signal sequence, a myelin basic protein encoding sequence (from bp 283 to 345, encoding amino acids 82 to 102), a β1 region of Class II MHC DR1β*1501 encoding sequence, a DNA sequence encoding a flexible linker, represented by the amino acid sequence (GGSGGS; SEQ ID NO:4), and an α1 region of Class II MHC DRA*0101encoding sequence. This plasmid was designed to direct secretion of a soluble, fused MHC heterodimer, denoted β1-α1, to which was attached, at the N terminus of β1, a myelin basic protein peptide that has been implicated in multiple sclerosis (Kamholz et al., Proc. Natl. Acad. Sci. USA 83: 4962–66, 1986).

To construct pLJ12, PCR was used to introduce a DNA sequence encoding MPB at the junction of the signal sequence and β1β2 sequence of the β chain of DR1β*1501. This was followed by joining the MBP-containing β1 region to the α1 region through a linker sequence which was introduced by PCR.

As a first step, the cDNA encoding a full length α chain, DRA*0101, and cDNA encoding a full length β chain were inserted into the expression vector pZCEP. DNA encoding these molecules may be isolated using standard cloning methods, such as these described by Maniatis et al. (Molecular Cloning: A Laboratory Manual, Cold Spring Harbor, N.Y., 1982; Sambrook et al., (Molecular Cloning: A Laboratory Manual, Second Edition, Cold Spring Harbor, N.Y., 1989); or Mullis et al., U.S. Pat. No. 4,683,195, which are incorporated herein by reference).

pZCEP (derived from pCDNAI (Invitrogen Inc., San Diego, Calif.)) was digested with Hind III and Eco RI, and a 0.85 kb Hind III-Eco RI fragment comprising the cDNA encoding β chain of DR1β*1501 was inserted. The resulting plasmid was designated pSL1.

pZCEP was digested with Bam HI and XbaI, and a ~0.7 kb SacI-SSPI fragment, comprising the cDNA encoding α chain of DRA*0101, was inserted along with a polylinker sequence containing Bam HI-SacI and SSPI-XbaI ends. The resulting plasmid was designated pSL2.

A cloning site was generated using PCR by amplifying a ~100 bp Hind III/ClaI fragment containing the signal sequence of Class II β DR1β*1501, to which a sequence encoding the first seven amino acids (DENVVH;SEQ ID NO:5) of MBP (82-104) was joined to the 3' end of the signal sequence. The DNA sequence encoding the amino acids VH was chosen to create a unique ApaLI site. A second ClaI/XbaI fragment of ~750 bp was generated using PCR, which contained a sequence encoding the β1β2 region and transmembrane domain of the Class II β chain DR1β*1501, to which was joined the DNA encoding the last two amino acids (GS) of the linker to the 5' end of the β1 sequence. The DNA sequence encoding the amino acids GS was chosen to create a unique Bam HI site.

The fragments were digested with Hind III/ClaI and ClaI/XbaI and inserted into Hind III/Xba I-digested pCZEP. The resulting shuttle plasmid was digested with ApaLI and BamHI, and oligonucleotides encoding the remaining portion of the MBP sequence (represented by the amino acid sequence (FFKNIVTPRTIPPS;SEQ ID NO:6)) and the start of the flexible linker (GGGSG;SEQ ID NO:7) were inserted. The resulting construct contained the MBP sequence joined to the β1β2 sequence of DR1β*1501 through an intervening linker. The resulting plasmid was designated pSL21.

To create pLJ12, a ~0.48 kb PCR fragment was generated which encoded the DNA sequence from the signal sequence through the β1 region of pSL21, onto which DNA encoding the sequence of a second flexible linker (represented by the amino acid sequence GASAG;SEQ ID NO:8) was joined. A second ~0.261 kb PCR fragment was created which encoded the α1 portion of DRA*0101, onto which the DNA encoding the second flexible linker was added to the 5' end, and a DNA sequence encoding a stop codon added to the 3' end. These two PCR fragments were used as PCR primers (overlapping sequences in the linker DNA and specific 5' and 3' primers), to produce a final Hind III/ XbaI PCR product which encoded the signal sequence of DR1β*1501 joined to the MPB peptide and linker peptide DNA, as described above. This was followed by β1, which was joined to the 5' end of α1 through DNA encoding the flexible peptide (GASAG;SEQ ID NO:8). This PCR product was introduced into Hind III/XbaI pZCEP and the resulting plasmid designated pLJ12.

Example 2

Protocol for Isolation and Propagation of GAD Reactive Human T Cell Clones

I. Isolation of Responder Cell Populations

Peripheral blood mononuclear cells (PBMNC), from pre-diabetic or new onset diabetic patents which should have a source of autoreactive T-cells, were isolated by density centrifugation on ficoll-hypaque. Cells were washed several times and resuspended in 15% PHS Medium (RPMI-1640, 15% heat inactivated normal male pooled human serum (from normal, non-transfused male donors, tested positive in a mixed lymphocyte culture using established techniques), 2 mM L-glutamine, and $5 \times 10^{-5}$ M beta-mercaptoethanol). A portion of the PBMNCs were saved to be used as antigen pulsed antigen presenting cells APCs (see below under stimulators), and a portion frozen for subsequent rounds of stimulation. The remainder were plated on tissue culture plates overnight at 37° C., 5% $CO_2$ to remove adherent cell populations.

A non-adherent cell population was harvested and enriched for T cells by passing cells over nylon wool, which removes monocytes and B cells. The cells which did not adhere were enriched for T cells and natural killer cells. The cells were further fractionated by removing CD56+ and CD8+ cells. This was done by collecting the non-adherent cells (depleted of CD56+ and CD8+) by sequential incubation of cells on anti-CD8 antibody coated plates and anti-CD56 antibody coated plates.

II. Preparation of Stimulator Cell Populations; Day 0

PBMNC (Approximately $10^7$ cells) were incubated in a 0.5 ml volume of 15% PHS media overnight at 37° C., 5% $CO_2$ with a 50 μg/ml GAD65. This can also be achieved using frozen cells which were thawed, washed 2× and incubated with GAD65 for 5–7 hours. The cells were irradiated with 3000 rads, washed 2× and counted.

III. Stimulation of T Cells

CD4+ T cells ($1.5 \times 10^6$) were mixed with $1.5 \times 10^6$ irradiated stimulators (from above) in 1.5 ml of 15% PHS medium. After 7 days, cells were harvested, washed 2× and restimulated with $1.5 \times 10^6$ stimulators which were prepared as described in II, using frozen autologous PBMNCs.

10 μl/ml human recombinant IL-2 (Research and Development Systems, Minneapolis, Minn.) was added to cultures on Day 11. Cultures were expanded as needed with medium, dividing 1:2 or 1:3 to keep cells at $<8 \times 10^5$ cells/ml. Additional IL-2 was added if cells were dividing too quickly or were in need of exogenous IL-2. On day 14, cells are restimulated, as above, to maintain the T cell line, and frozen stocks were created. T cell clones were created at this time through limiting dilution.

IV. Cloning of T Cells

On day 14, T-cells were harvested, washed, resuspended in 15% PHS medium with 10 μl/ml IL-2, and plated with $1 \times 10^4$ stimulators (as prepared above) in terasaki plates (Research and Development Systems) in 15 μl total volume. Cloning can alternatively be started on day 7.

Cells were inspected for growth and transferred to wells, with the cell volume being about ½ of the well volume of a 96 well round bottom plate, in 200 μl 15% PHS medium containing $1 \times 10^5$ stimulators. An additional aliquot of IL-2, to a final concentration of 10 μl/ml of 15% PHS medium, was added to the cultures 24 hours later.

As cells grew in the wells, they were tested for antigen reactivity on days 4 or 5, and were split 1:2 into additional wells containing 10 μl/ml 15% PHS medium as the cells become confluent.

Cells stocks were frozen from 96 well cultures or were expanded into 24 well, 1.5 ml cultures using T cells from 1 or several of the above wells and $1.5 \times 10^6$ stimulators.

V. Testing Reactivity to GAD

T-cell clones were rested (not given IL-2 for 2 days, at least 7 days post-stimulation with antigen), washed, counted and resuspended in 15% PHS medium. They were plated at 25,000 cells/well in 100 μl 15% PHS medium. Autologous or HLA-class II-matched PBMNCs are loaded with GAD by incubating with GAD (about 50 μg/ml) for at least 5 hours. The cells are washed and irradiated with 3000 rads. These cells are washed and resuspended in 15% PHS medium, and added to the T-cells at a concentration of $1 \times 10^6$ cells/well in 100 μl 15% PHS medium. The cells were incubated for 48 hours, then pulsed with 1 μCi 3H-thymidine and harvested. A positive response is considered to be a stimulation index >3 (stimulation index SI=average cpm of sample stimulated with antigen/average cpm of sample of cells stimulated with no antigen or control antigen). Some controls include T-cells alone, and stimulators alone.

Other methods, well known in the art, for testing clones include dose response to antigen; response to these antigens or negative antigen controls; determination of HLA-class II restriction by adding blocking anti-HLA class II antibody to plates; and use of peptides to load stimulators to determine peptide specificity, which can be done as described above, with shortened incubation period (2 hours) and concentration of peptides 10 μM (10 μg/ml). A dose response in combination with peptide specificity tests can also be done.

Example 3

Synthesis of GAD Peptides

Peptides amidated at the C terminus were synthesized by solid phase peptide synthesis (SPPS) using Fmoc chemistry. Chemicals used in the synthesis were obtained from Nova Biochem (La Jolla, Calif.). The peptide was assembled on Rink amide MBHA resin (0.25 millimolar scale) starting from the C terminal end by using a 432A Applied Biosystems, Inc. (Foster City, Calif.) automated peptide synthesizer and solid phase strategy. The synthesis required double coupling to ensure completion of the coupling reaction, and HBtu-HOBt coupling chemistry was used. Bolded residues required at least double coupling (SRLSKVAPVIKARMMEYGTT-NH2 (SEQ ID NO:3). Each cycle included Fmoc deprotection of amine from the amino acid residue on the resin, and coupling of incoming Fmoc-amino acid. After successful assembly of the peptide, the resin was washed with dichloromethane and dried under vacuum for two hours. The peptide resin was resuspended in 10 ml trifluoroacetic acid (TFA) containing 1 ml of 4-methoxybenzenethiol and 0.7 g of 4-methylmercaptophenol as scavengers. The suspension was gently mixed at room temperature for 2 hours, then filtered through a PTFE filter, and the filtrate was collected in a capped glass bottle containing 1 liter organic solvent mixture (pentane:acetone=4:1). The white precipitate was allowed to settle at room temperature for 1–2 hours, after which the crude precipitated peptide was isolated by cacantation centrifugation. The crude peptide was washed three times with the organic solvent mixture and dried under vacuum overnight.

Reverse phase HPLC of the crude peptide showed a main peak and smaller impurities which may be deletion peptides. The main peak was isolated by preparative reverse phase HPLC using a solvent gradient consisting of starting buffer A (0.1% TFA) and ending buffer B (70% acetonitrile in 0.1% TFA). Fractions were collected (10–15 ml) and lyophillized to remove all solvent. Fractions were analyzed by reverse HPLC and the pure fractions were further characterized by mass spectrometry.

Peptides having a carboxylic group at the last amino acid at the C-terminus were prepared using solid phase Fmoc chemistry. Peptides were assembled on Wang resin starting from the C-terminal end by using a 431A Applied Biosystems automated peptide synthesizer. Wang resin with the first amino acid attached (Fmoc-Thr(tBu)-Wang) was loaded in the synthesizer, and the couplings were done from the next amino acid at the C-terminus. Double couplings, on those amino acids as indicated above, were done to ensure completion of the coupling reaction. HBtu-HOBt coupling chemistry was used for this purpose. Each cycle included Fmoc deprotection of amine from the amino acid residue on the resin and coupling of incoming Fmoc-amino acid. After successful assembly of the peptide, the resin was washed with dichloromethane and dried for two hours. Cleavage and purification of the peptide is as described above.

Example 4

Characterization of Antigentic Peptides

In order to identify the diabetictogenic GAD65 peptide, several peptides were synthesized with either an acid-OH or basic-$NH_2$ C-terminus, including GAD65 #17-$NH_2$ NMYAMMIARFKMFPEVKEKG-$NH_2$ 247–266 (SEQ ID NO:/1), GAD65 #34-$NH_2$ VPPSLRTLEDNEERMSRLSK-$NH_2$ 509–528 (SEQ ID NO:/2) and GAD65 #35-$NH_2$ SRLSKVAPVIKARMMEYGTT-$NH_2$, 524–543 (SEQ ID NO: 3).

As another tool, the cell line AG7D was created by fusing NOD spleen cells with a B lymphoma line A20. AG7D thus expresses both I-$A^{g7}$ from the NOD background and I-$A^d$ from the A20 background.

The relative affinity of a given peptide for MHC was measured by a Europium-streptavidin dissociation enhanced lanthanide fluoroimmunoassay (DELFIA), as developed by Jensen et al., J. Immunol. Meth. 163: 209, 1993. This assay can be used with either whole cells or solublized MHC molecules. In both cases, the material was incubated overnight at 37° C. at pH 5.5 with titered biotinylated peptide; if whole cells were used, they were lysed the next day. The MHC:peptide complexes were added to 96 well plates precoated with anti-MHC monoclonal antibody, washed to remove unbound material, incubated with Europium-avidin, washed and measured on a Wallac 1234 DELFIA Research Fluorometer. Mouse serum albumin (MSA), a known allele-specific peptide with high affinity for I-$A^{g7}$, was used as a positive control, and Eα, which binds to I-$A^d$ but not to I-$A^{g7}$, served as a negative control.

Using the AG7D hybridoma, two peptides were chosen as allele specific controls. I-$A^{g7}$ is restricted to MSA-OH (the NOD mouse Class II MHC molecule), and does not bind peptide Eα-OH. I-$A^d$ is restricted to Eα-OH, and does not bind peptide MSA-OH. Biotinylated GAD65 #35-$NH_2$ (SEQ ID NO:/3) is a stronger binder to I-$A^{g7}$. It is not restricted to this MHC, however, as it also binds I-$A^d$. Unexpectedly, an alteration from a basic to an acidic C terminus of the peptide caused a decrease in MHC binding. Native MHCs harvested from NOD and BALB/c spleen cells were also tested. Again, each GAD65 peptide was screened for binding, and the results paralleled those seen with AG7D cell surface MHC. The same results were again seen when corresponding soluble MHC was assayed. Again, GAD65 #35-$NH_2$(SEQ ID NO:/3) bound most strongly. However, soluble MHC also binds GAD65 #17-OH.

Affinity-purified I-$A^{g7}$ (at a concentration of 5–10 μg/ml) was incubated with biotinylated-GAD peptides at 37° C. for 96 hours at optimized pH for quantitation of bound peptide. The resulting MHC:peptide complex preparations were analyzed by antibody capture plate assay using an enzyme-conjugated avidin system, as described above, with the following modifications: Purified polyclonal antibody against I-$A^{g7}$ was at a concentration of 4 μg/100 μl, and BSA-biotin ranged from 0.014–1.8 pmoles (0.117–5 mg) and was used to coat a 96 well microtiter plate (Nunc Poly-Sorb, Baxter) overnight at 4° C. Plates were blocked with 1% fish gelatin. I-$A^{g7}$:biotin peptide complexes so prepared were applied to the wells in duplicate, ranging from 12.5–200 ng (0.21–3.32 pmoles) in appropriate dilution buffers and incubated for 2 hours at room temperature. The wells were washed three times with PBS containing 0.01% TWEEN-20 to remove unbound peptide. Bound biotinylated peptide was detected colorimetrically using alkaline phophatase-conjugated streptavidin and p-nitrophenyl phosphate (disodium) in 0.1 M diethanolamine as a substrate. Wells were read at 405 nm in a microtiter plate reader (Molecular Devices). The percent of I-$A^{g7}$ having bound peptide was calculated using a BSA-biotin (8 biotin molecules per BSA) standard curve. Equivalent amounts of biotinylated peptides in the absence of MHC Class II antigens were used as controls, and showed less than 1% non-specific binding in the plate assay. Control values were subtracted for calculating the percent peptide occupancy. GAD65 #35-$NH_2$ showed greater than 60% bound peptide at a molar excess of 100, whereas the control and the carboxylated peptides achieved only 10%, at up to 500 molar excess.

To demonstrate the proliferative recall response of in vivo primed T lymphocytes to a secondary in vitro stimulation, seven-week old female NOD mice were injected in the footpad with 50 μg peptide in 100 μl complete Freund's Adjuvant (CFA); two mice each received GAD65 #35-NH2 or GAD 65 #35-OH. After eight days, mice were sacrificed. The lymph nodes and spleens were removed, and tissues were ground between glass slides to free the lymphocytes. Red blood cells were lysed with water, followed by addition of 1× PBS. Cells were plated in 96 well microtiter plates at 1×$10^6$ cells/well and tested against each of the three GAD65 peptides. Peptide concentration was titered from 1000 μg/ml to 0.45 μg/ml. Neither cells primed with GAD65 #17 nor GAD65 #34 showed a response in the secondary in vitro stimulation with that peptide, while cells primed with GAD65 #35 showed a significant recall response against the same peptide.

Example 5

Creation of GAD65 #35-NH2 Hybridoma Cell Line MBD.1

A hybridoma cell line that expresses T cell receptors specific to GAD65 #35-NH2 has been created. The procedure is derived from "Production of Mouse T Cell Hybridomas" in *Current Protocols in Immunology*, Wiley Interscience, Greene. Briefly, three nine-week old female NOD mice were injected with 50 μg GAD65 #35-NH2 in 100 μl CFA to cause proliferation of T cells restricted to this peptide. Lymph nodes and spleens were removed eight days later. Tissues were ground and red blood cells were lysed with water, followed by the addition of 10× PBS. Cells were again stimulated with peptide in vitro to encourage proliferation of restricted T cells. Once cells entered the blast stage, dead cells were removed by centrifugation over Ficoll-Hypaque. Viable cells were combined in a 1:1 ratio with BW5147 cells, a lymphoma line. After centrifugation, the supernatant was removed, and 50% PEG solution was added to the pellet dropwise over several minutes to cause cell fusion. This mixture was washed and centrifuged in medium containing no fetal bovine serum. Thymocytes in medium with 20% FBS were then added to the aspirated pellet. The cells were then plated in 96 well microtiter plates, leaving the outside wells empty to ensure sterility. The next day, 100 μl 2× HAT selection medium was added, causing the death of fusions between two lymphoma cells. The death of fusions of two lymphocytes occurs passively. Thus, only fusions between one lymphoma and one lymphocyte survive. On day six, cells were placed in fresh 2× HAT medium. In the days following, cells were checked for expansion. Those appearing to grow were maintained and then screened for specificity to GAD65 #35-NH2.

To screen for specificity, NOD antigen presenting cells were plated at $5 \times 10^3$ cells/well in the presence of titered GAD 65 #35-$NH_2$ peptide. Hybridomas with potential specificity for the GAD 65 #35-$NH_2$ peptide were added at $1 \times 10^5$ cells/well. These were incubated overnight at 37° C., 5.0% $CO_2$. The supernatant, which contains IL-2 only in the case of responder T-hybridoma proliferation, was removed the next day and frozen to kill any remaining cells. CTLL cells, which are dependent upon IL-2 for survival, were plated, and 50 μl of the supernatant was added. This culture was incubated overnight, at which point cells were pulsed with tritiated thymidine. After incubating, cells were harvested in a Skatron Basic 96 Cell Harvester, and incorporation of $^3$H-thymidine into CTLL DNA was measured on a Wallac 1205 Betaplate Beta Counter (Turku, Finland). The T cell hybridoma, MBD.1, showed a strong proliferative response to GAD65 #35-NH2, indicating that it is specific to this peptide.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

We claim:

1. A method for preparing a CD56 negative, CD8 negative responder cell clone that proliferates when combined with a selected antigenic peptide presented by a stimulator cell, comprising:

isolating CD56 negative, CD8 negative cells comprising the steps of:
   plating peripheral blood mononuclear cells to separate adherent cells from non-adherent cells,
   passing said non-adherent cells over nylon wool, wherein the flow-through is enriched for T cells,
   incubating said flow-through enriched for T cells with antibodies to CD56 and CD8 to remove CD56 positive, CD8 positive cells,
   thereby forming CD56 negative, CD8 negative responder cells;
   stimulating the CD56 negative, CD8 negative responder cells with pulsed or primed stimulator cells;
   restimulating the stimulated CD56 negative, CD8 negative responder cells with pulsed or primed stimulator cells; and
   isolating a CD56 negative, CD8 negative responder cell clone that proliferates when combined with a selected antigenic peptide presented by a stimulator cell.

2. The method of claim 1, wherein the responder cells are isolated from a prediabetic or new onset diabetic patient.

3. The method of claim 1, wherein the responder cell clone is a T cell clone.

4. The method of claim 1, wherein the selected antigenic peptide is a GAD65 peptide.

* * * * *